(12) United States Patent
Wu et al.

(10) Patent No.: US 6,548,709 B2
(45) Date of Patent: Apr. 15, 2003

(54) METHOD FOR THE PRODUCTION OF ARYLSULFIDES AND COMPOSITIONS MADE THEREFROM

(75) Inventors: Margaret M. Wu, Skillman, NJ (US); Philip Trotto, Yarley, PA (US); Shifang Luo, Jamison, PA (US); Jose G. Santiesteban, Bethlehem, PA (US); Hye Kyung C. Timken, Albany, CA (US); Sandeep S. Dhingra, Midland, MI (US); Simon C. Weston, Annadale, NJ (US); Richard T. Spissell, National Park, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/973,606

(22) Filed: Oct. 9, 2001

(65) Prior Publication Data

US 2002/0137971 A1 Sep. 26, 2002

Related U.S. Application Data

(63) Continuation of application No. 09/473,597, filed on Dec. 29, 1999, now abandoned.
(60) Provisional application No. 60/114,242, filed on Dec. 30, 1998.

(51) Int. Cl.$^7$ .............................................. C07C 319/00
(52) U.S. Cl. ........................................... 568/58; 568/38
(58) Field of Search ...................................... 568/38, 58

(56) References Cited

U.S. PATENT DOCUMENTS

| | | | | |
|---|---|---|---|---|
| 3,706,805 A | * | 12/1972 | Fujisawa et al. | |
| 4,740,292 A | | 4/1988 | Chen et al. | 208/120 |
| 4,792,634 A | * | 12/1988 | Rule | 568/58 |
| 4,891,448 A | * | 1/1990 | Garces et al. | 568/628 |
| 4,898,982 A | | 2/1990 | Hussmann | 568/58 |
| 5,107,049 A | | 4/1992 | Le et al. | 585/467 |
| 5,344,578 A | | 9/1994 | Wei et al. | 252/47.5 |
| 5,955,404 A | | 9/1999 | Horodysky et al. | 508/294 |

OTHER PUBLICATIONS

CA:128:61467 abs of Chinese Chem Lett by Zuo et al 8(10) pp 849–852 1997.*
CA:94:15323 abs of Katal. Sint. Org. Soedin Sery by Gadzhiev et al pp. 194–196 1979.*
CA:124:288893 abs of Sulfur Lett by Clark et al 19(1) pp. 17–22 1995.*

* cited by examiner

Primary Examiner—Jean F. Vollano
(74) Attorney, Agent, or Firm—Louis N. Moreno

(57) ABSTRACT

The present invention relates to methods for production of arylsulfides wherein an aromatic compound is reacted with elemental sulfur in the presence of solid acid catalyst. The solid acid catalyst can be a zeolite. The methods are useful for producing alkylated diphenylsulfides from aromatic compounds and elemental sulfur.

21 Claims, 4 Drawing Sheets

METHOD FOR THE PRODUCTION OF ARYLSULFIDES AND COMPOSITIONS MADE THEREFROM

CROSS-REFERENCE TO RELATED APPLICATION

This application claims the benefit of priority and is a continuation of U.S. Ser. No. 09/473,597, filed Dec. 29, 1999, now abandoned, with claims benefit of U.S. Provisional Application Ser. No. 60/114,242, filed Dec. 30, 1998.

FIELD OF THE INVENTION

The present invention relates to methods for the production of arylsulfides and to compositions made therefrom. In particular, the present invention relates to methods for the production of arylsulfides from the reaction of an aromatic compound with elemental sulfur in the presence of a solid acid catalyst, and to compositions made therefrom.

BACKGROUND OF THE INVENTION

Arylsulfides are beneficial as lubricants, additives, solvents, and as intermediates to lubricant base stocks, drugs, and agricultural chemicals. A particularly desired arylsulfide is diphenlysulfide (DPS), a molecule with two benzene rings linked by a sulfur atom. DPS is a high-valued chemical that is used in the synthesis of alkylated diphenylsulfides (ADPSs), a family of high-performance synthetic hydrocarbon fluids useful in engine oil formulations. In addition, DPS is used as a starting material for the preparation of 4,4'-bis(chlorobenzene)sulfone, a monomer used in the production of high-performance thermoplastic polysulfones.

DPS can be prepared from benzene, sulfur monochloride, and aluminum chloride according to the following reaction scheme:

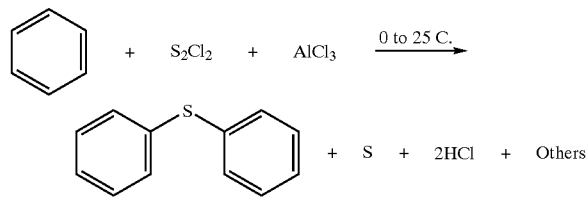

Other routes for the large scale production of DPS have been described. For example, synthetic routes for the production of DPS have been described which use the high-temperature thermal reaction of chlorobenzene with hydrogen sulfide or the reaction of benzene with sulfur using stoichiometric amounts of $AlCl_3$ or zeolites in a batch-type reactor.

In addition, the production of DPS via an acid-catalyzed reaction between benzene and sulfur was first reported by Friedel and Crafts. The reaction is believed to proceed through an aromatic electrophilic substitution mechanism. The acid catalyst enhances the electrophilicity of sulfur via the formation of positively charged sulfur intermediates. These intermediates are believed to be produced by the formation of a Lewis acid-base adduct between sulfur and the Lewis acid or by the protonation of sulfur by a Bronsted acid. Products of the reaction include DPS, thiophenol, diphenyldisulfide (DPDS), thianthrene (TT), and phenylenesulfide oligomers and polymers, with the distribution of products depending strongly on the molar ratio of benzene and sulfur.

However, none of the known routes provide an adequate commercial source of DPS. Rather, the known processes suffer from numerous drawbacks, including, for example, the use of corrosive reactants (e.g., halogenated hydrocarbons), the production of corrosive by-products (e.g., gaseous hydrochloric acid), poor selectivity (e.g., the production of significant amounts of phenylenesulfides and chlorinated compounds, such as chlorobenzene), the need for extensive downstream separations (e.g., separation of catalyst from the product stream), and the generation of large amounts of benzene-containing catalyst waste. Similar problems have been encountered in the production of other phenyl sulfides, such as the thianthrenes.

These drawbacks have negative implications for the commercial use of ADPSs. The commercial use of ADPSs has been hampered by the need to purify the DPS prior to use as a reactant in the formation of the ADPSs. In particular, the poor selectivity for DPS and the presence of high concentrations of corrosive by-products made it imperative that the DPS be removed from the product stream prior to use. However, the purification of the DPS is expensive and time consuming.

In light of the foregoing, the large scale production of DPS has been expensive. Further, the high cost of producing the starting material DPS has prevented the ADPSs from being commercialized.

Accordingly, it would be highly beneficial to provide a method for the large scale production of arylsulfides. The method should provide for the production of arylsulfides in large yield without the use of highly corrosive reactants. Further, the method should produce little or no corrosive and/or undesired by-products. In addition, the method should utilize readily available reactants and be selective.

SUMMARY OF THE INVENTION

The drawbacks associated with the known methods for producing arylsulfides is overcome, to a large extent, by methods in accordance with the present invention. The present invention provides a method for producing arylsulfides wherein an aromatic compound and sulfur are reacted in the presence of an acidic catalyst. The reaction is very clean and produces little undesirable by-products. Usually, high sulfur conversion and selectivity to arylsulfides can be obtained under mild reaction conditions. The method can be used to produce arylsulfides in large scale and at economical prices.

In one of its aspects, the present invention relates to methods for the production of arylsulfides wherein an aromatic compound is reacted with elemental sulfur in the presence of a solid acid/oxide catalyst. The aromatic compound can be alkylated. In a preferred embodiment, the acid catalyst is a molecular sieve, preferably a zeolite such as MCM-56, ZSM-5, MCM-22, MCM-68, and USY. The reaction is optionally performed in a fixed-bed reactor.

In another of its aspects, the present invention relates to methods for the production of alkylated diphenylsulfides wherein an alkylated aromatic compound is reacted with elemental sulfur in the presence of a solid acid catalyst. In a preferred embodiment, the acid catalyst is a zeolite, such as MCM-56, ZSM-5, MCM-22, MCM-68, and USY. The reaction is optionally performed in a fixed-bed reactor.

In yet another of its aspects, the present invention relates to methods for the production of alkylated diphenylsulfides wherein an aromatic compound is reacted with elemental sulfur and an alkylating agent in the presence of a solid acid catalyst. The alkylating agent is preferably an olefin, more preferably a $C_6$ to $C_{20}$ olefin, and most preferably a $C_{10}$, to $C_8$ alpha olefin such as dodecene-1, decene-1, and tetradecene-1. In a preferred embodiment, the acid catalyst is a zeolite, such as MCM-56, ZSM-5, MCM-22, MCM-68, and USY.

Additional features and embodiments of the present invention will become apparent to those skilled in the art in view of the ensuing disclosure and appended claims.

BRIEF DESCRIPTION OF THE DRAWINGS

The numerous objects and advantages of the present invention may be better understood by those skilled in the art by reference to the accompanying detailed description and the following drawings, in which.

DETAILED DESCRIPTION OF THE INVENTION

Figure 1:
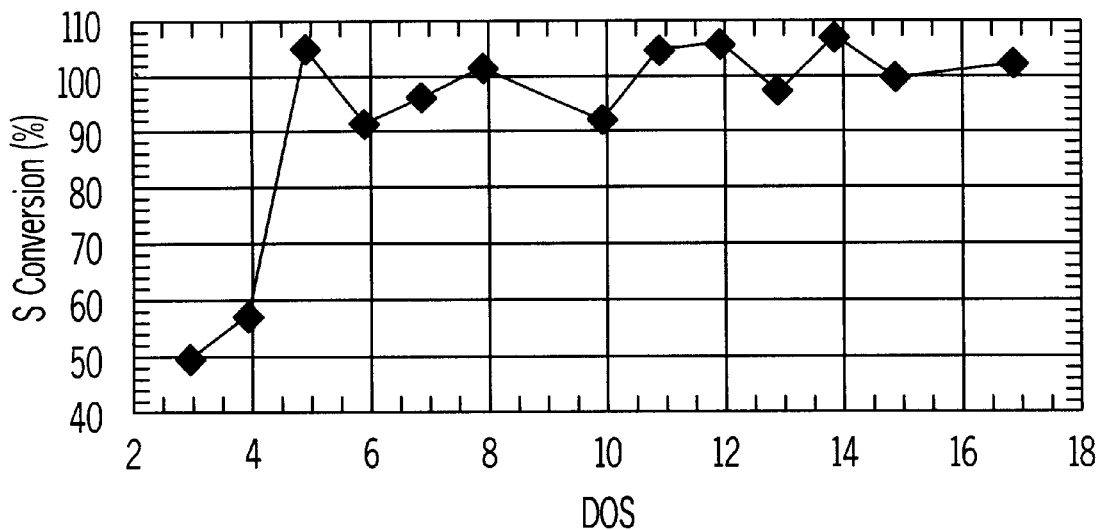
FIG. 1 is a graph showing sulfur conversion in percent as a function of days on stream (DOS) for the reaction of benzene with sulfur in the presence of MCM-56 catalyst at 300° C., 500 psig, 1 WHSV, and a benzene to sulfur mole ratio of 20:1.

The present invention relates to methods for the production of arylsulfides. The arylsulfides are produced by reacting an aromatic compound with elemental sulfur in the presence of a solid acid catalyst. The methods enable the production of a variety of arylsulfides, including polyarylsulfides, aryldisulfides, and polyaryldisulfides. Additionally, the methods can be used to produce substituted arylsulfides, including alkylated arysulfides.

Suitable aromatic compounds include benzene, toluene, biphenyl, xylene, hemimellitene, pseudocumene, ethylbenzene, n-propylbenzene, cumene, n-butylbenzene, isobutylbenzene, sec-butylbenzene, tert-butylbenzene, p-cymene, biphenyl, diphenylmethane, triphenyl methane, 1,2-diphenylethane and similarly alkyl substituted naphthalenes and anthracenes; also derivatives of aromatic hydrocarbons including phenol, hindered phenols such as 2,6-dimethyl phenol, catechol, acylphenol such as acetylphenol, carbonate esters such as phenyl methyl or ethyl carbonate and diphenyl carbonate, alkylphenol such as anisole, chloro and bromobenzene, aniline, acyl aniline such as acetanilide, methyl and ethylbenzoate, thiophenol and acylated thiophenol, nitrobenzene, diphenylether, diphenylsulfide and similarly substituted naphthalenes and anthracenes, in particular naphthols such as mono and dihydroxy naphthalene. A particularly preferred aromatic compound is benzene. For applications where stability in hydrocarbons is desired (e.g., lubricant additives), alkyl substituents, and especially $C_8$–$C_{20}$ alkyl substituents, are preferably present.

The sulfur is in its elemental form and can be used without further purification. The sulfur can be combined with the aromatic compound to form a saturated sulfur solution. Toward that end, the sulfur can be dissolved within a liquid solution containing the aromatic compound. For example, when the aromatic compound is benzene, an appropriate amount of sulfur can be dissolved directly in an appropriate amount of benzene to provide a benzene/sulfur solution having the desired mole ratio of benzene to sulfur.

The reaction between the aromatic compound and the sulfur is carried out in the presence of solid acid catalyst. The acid catalyst can be aluminum chloride ($AlCl_3$), $BF_3$, $AlBr_3$, solid zeolite, a layered catalyst, or any of a variety of other molecular sieves. Examples of suitable zeolite catalysts include MCM-56, ZSM-5, MCM-22, MCM-68, and USY. Zeolites may be used with framework metal elements other than aluminum such as, for example, boron, gallium, iron, and chromium.

When a zeolite is used, the zeolite preferably has a pore size of at least 5 Å. Large pore size zeolite catalysts are usually preferred, although less highly constrained medium or intermediate pore size zeolites may also be used. Generally, the large pore size zeolites are characterized by a pore structure with a ring opening of at least about 7 Å and the medium or intermediate pore size zeolites with a ring structure of 10 memebered oxygen ring systems will have a pore opening smaller than about 7 Å but larger than about 5.6 Å. Examples of suitable large pore size zeolites include zeolites such as faujasite, synthetic faujasites (zeolite X and Y), zeolite L, ZSM4, ZSM-18, ZSM-20, mordinite and offretite which are characterized by the presence of a 12-membered oxygen ring system in the molecular structure as described in Chen et al, "Shape-Selective Catalysis in Industrial Applications", Chemical Industries Vol. 36, Marcel Dekker Inc., New York, 1989. The large pore zeolites are preferably characterized by a "Constraint Index" of not more than 2, in most cases not more than 1. Zeolite beta is included in this class although it may have a "Constraint Index" approaching the upper limit of 2. The method for determining Constraint Index is described in U.S. Pat. No. 4,016,218 together with values for typical zeolites. The significance of the Constraint Index is described in U.S. Pat. No. 4,816,932 to which reference is made for a description of the test procedure and its interpretation.

A highly useful large pore zeolite for the production of the arylsulfides of the invention is zeolite Y in the ultrastable form, usually referred to as USY. Zeolite USY or zeolite Y, is a material of commerce, available from W. R. Grace & Co. and other suppliers, in large quantities as a catalyst for the cracking of petroleum. Zeolite Y may be bound with silica, alumina, silica-alumina or other metal oxides. It may typically have a $SiO_2^-$ to $Al_2O_3$ ratio of from 3–500, and be partially exchanged with rare earth elements, with ammonium cation or with other cations. Reference is made to Wojoiechowski, "Catalytic Cracking: Catalysts, Chemistry and Kinetics", Chemical Industries Vol. 25, Marcel Dekker, New York, 1986, for a description of zeolite USY, its preparation and properties.

Examples of useful medium pore size zeolites include the pentasil zeolites such as ZSM-5, ZSM-22, ZSM-23, and ZSM-35, as well as other zeolites such as ZSM-50, ZSM-57, MCM-22, MCM-49, MCM-56, MCM-68, all of which are known materials. Zeolite MCM-22 is described, for example, in U.S. Pat. No. 4,954,325 to M. K. Rubin and P. Chu. MCM-56 is described, for example, in U.S. Pat. Nos. 5,632,697; 5,453,554; 5,557,024; 5,536,894; and 5,827,491. MCM-68 is described, for example, in U.S application Ser. No. 09/234,544, filed Jan. 21, 1999. All of the above patents and applications are hereby incorporated by reference in their entireties.

The zeolite catalyst is optionally pretreated. Pretreatment of the catalyst flows from the discovery that zeolite catalysts which are low in moisture content, water-of-hydration content and absorbed-oxygen content consistently produce compositions that have improved color and excellent oxidative and thermal stability. Commercially obtained zeolite catalysts have been found to be relatively rich in moisture content, water-of-hydration content and absorbed-oxygen content. Reducing the moisture content, water-of-hydration content and absorbed-oxygen content of the commercially obtained zeolite catalyst by pretreatment has been found to yield a superior product.

The zeolite catalyst is pretreated by heating the solid catalyst particles for a time sufficient to lower the catalyst water content, water-of-hydration and absorbed oxygen content. Preferably and conveniently, the solid catalyst is heated in a vessel in bulk form but it is within the scope of the present invention to suspend the catalyst in an otherwise unreactive and inert liquid, with or without stirring, to enhance heat transfer to the solid catalyst and accelerate pretreatment. Vapor of the inert liquid may be removed periodically to carry off water vapor and oxygen from the catalyst. However, the zeolite catalyst is pretreated preferably by heating the solid catalyst in an inert gaseous environment at a temperature and for a time sufficient to lower the catalyst water content, water-of-hydration and absorbed oxygen content. Most preferably, the pretreatment is carried out in a vessel employing a moisture-free inert gas purge stream, such as nitrogen or Group VIII gases of the Periodic Table, to remove water vapor and oxygen from the vessel. Optionally, the pretreatment may be carried out by heating the catalyst in vacuo in a closed vessel.

To those skilled in the chemical engineering arts, other means are well known to essentially dry solid particles by continuous or batchwise methods. These methods are included within the scope of the present invention to the extent that they can be applied to remove water, water-of-hydration and absorbed oxygen from solid zeolite catalyst particles. The zeolite catalyst can be pretreated in a fixed bed, fluid bed or batchwise. Rather than employing a vessel, the solid catalyst particles can be transported through a column containing an inert liquid at an appropriate temperature or the solid can be carried through a heated or inert liquid-containing column by gas ebullition.

The water content, water-of-hydration and absorbed oxygen content of the zeolite catalyst particles can be effectively lowered by heating the catalyst at a temperature between 50° C. and 500° C., but preferably at a temperature between about 200° C. and about 400° C. The catalyst is heated for between about 0.5 hours and about 24 hours and, preferably, between about 1 hour and about 5 hours. However, at a preferred temperature of about 300° C. in a vessel in the presence of a nitrogen purge stream, about two hours of heating has been found sufficient to pretreat the catalyst particles.

As an alternative to the zeolites, other molecular sieves may be used. Examples of useful, non-zeolite molecular sieves include the silicates (e.g., metallosilicates, titanosilicates) of varying silica-alumina ratios; metalloaluminates (e.g., germaniumaluminates); metallophosphates; aluminophosphates (AlPO; e.g., the silico- and metalloaluminophosphates referred to as metal integrated aluminophosphates (MeAPO and ELAPO); metal integrated silicoaluminophosphates (e.g., MeAPSO and ELAPSO); and silicoaluminophosphates (SAPO)); and gallogermanates. Without intending to be bound by theory, it is believed that use of the non-zeolite molecular sieves may not be as favorable since it appears that some acidic activity (as conventionally measured by the alpha value) is desired for optimum performance. A discussion of the structural relationships of SAPOs, AlPOs, MeAPOs, and MeAPOs may be found in a number of resources including Stud Surf Catal., 37:13–27 (1987). The AlPOs contain aluminum and phosphorus, while in the SAPOs some of the phosphorus and/or some of both the phosphorus and aluminum is replaced by silicon. In the MeAPOs, various metals are present, such as Li, B, Be, Mg, Ti, Mn, Fe, Co, An, Ga, Ge, and As, in addition to aluminum and phosphorus, while the MeAPSOs additionally contain silicon. The negative charge of the $Me_aAl_bP_cSi_dO_e$ lattice is compensated by cations, where Me is magnesium, manganese, cobalt, iron, and/or zinc. MeAPSOs are described in U.S. Pat. No. 4,793,984. SAPO-type sieve materials are described in U.S. Pat. No. 4,440,871. MeAPO-type catalysts are described in U.S. Pat. Nos. 4,544,143 and 4,567,029. ELAPO catalysts are described in U.S. Pat. No. 4,500,651 and ELAPSO catalysts are described in European Patent Application No. 159,624. Specific molecular sieves are described, for example, in the following patents: MgAPSO and MgAPSO in U.S. Pat. No. 4,758,419; MnAPSO in U.S. Pat. No. 4,686,092; CoAPSO in U.S. Pat. No. 4,744,970; FeAPSO in U.S. Pat. No. 4,683,217; and ZnAPSO in U.S. Pat. No. 4,935,216. All of the above patents and applications are hereby incorporated by reference in their entireties. Specific silicoaluminumphosphates which may be used include SAPO-11, SAPO-17, SAPO-34, and SAPO-37. Other specific sieve materials include MeAPO-5 and MeAPSO-5.

The method of the invention is carried out by contacting the aromatic compound, sulfur and the catalyst in a suitable reaction zone which may be a fixed catalyst bed, fluid bed or stirred reactor vessel. The mole ratio of the aromatic compound to sulfur is preferably between about 50:1 and about 0.1:1 and, more preferably, between about 25:1 and about 10:1 to provide sufficient diluent for the reaction. A mole ratio of higher than about 50:1 detrimentally affects the reaction by dilution. If the mole ratio is below about 1:1, excess unreacted aromatic may remain.

The time for which the aromatic compound and the sulfur are contacted can vary. In general, contact is maintained for a time sufficient that the aromatic compound and the sulfur react to a desired level of completion. For example, contacting time can vary from several minutes to several hours or more.

The temperature which is maintained during the reaction of the aromatic compound and the sulfur can vary. In general, it is preferred to carry out the reaction at the lowest temperature which will provide for the desired efficiency of reaction. For example, suitable temperatures can range from about 20° C. to about 300° C. Preferably, the reaction is carried out at, or slightly above, ambient room temperature. "Room temperature", as used herein, includes temperatures from about 20° C. to about 30° C., preferably about 25° C.

The pressure maintained during the reaction between the aromatic compound and the sulfur can also vary. Appropriate pressures to provide efficient formation of arylsulfide product can be readily determined by one of skill in the art. For example, suitable pressures can range from about ambient pressure to about autogenous reaction pressure at the selected temperature. However, higher pressures can be used, for example up to about 1000 psig (68 atm). Preferably, the pressure is between about 400 psig (27.2 atm) and about 600 psig (40.8 atm).

The fixed bed weight hourly space velocity (WHSV) can also be varied. Appropriate values for the WHSV are between about 0.1 $hr^{-1}$, and about 10 $hr^{-1}$, preferably between about 0.1 $hr^{-1}$ and about 2 $hr^{-1}$, and more preferably between about 0.1 $hr^{-1}$ and about 1 $hr^{-1}$. A WHSV above about 10 $hr^{-1}$ is detrimental because of the short residence time. A WHSV below about 0.01 $hr^{-1}$ results in low productivity.

EXAMPLES

The reaction of benzene and sulfur over five zeolite catalysts was studied. Benzene (HPLC Grade, EM Science) was percolated through an $Al_2O_3$ (activated at 500° C.) column at ambient conditions prior to use. Sulfur powder (sublimed, 99.99%; Baker) was dried in an oven at 100° C. before use. The reactions were conducted in a stainless steel, down-flow, fixed-bed microprocessing reactor. A saturated sulfur solution in benzene (2 weight percent) was prepared by mixing sulfur and benzene in proper proportions (17.5 g sulfur in 874 g benzene) in a volumetric flask and stirring the slurry until a homogeneous solution was obtained at room temperature. The reactor was loaded with 2.0 g catalyst in a powder form (60–80 mesh, with sand) and heated to 300° C. under a continuous $N_2$ flow (approximately 100 mL/min) for 2 hours. The reactor pressure was then increased to 500 psig (34.0 atm). The saturated sulfur solution was warmed to 50° C. and fed to the reactor at a flow rate of 60 cc/hour for 1 hour. The temperature of the reactor was gradually increased to 300° C. Material balances were started after a 24 hour lineout period.

The reaction product mixtures were analyzed using gas chromatography on a Varian 3700 Gas Chromatograph with a DB-1 column (60 m×0.33 mm×1 μm; J&W Scientific). In addition, gas chromatography-mass spectroscopy analyses were performed on an HP 5890 Series III Gas Chromatograph with an SPB-1 column (60 m×0.32 mm×1 μm; Supelco). Sulfur analyses were conducted with an HP 5890 Series II Plus GC instrument equipped with an Altech column (10 m×0.53 mm×1.2 μm) and a sulfur chemiluminescence detector (Sievers 355).

The zeolite catalysts utilized were MCM-56, ZSM-5, MCM-22, MCM-68, and USY. The physical properties of each of these catalysts are listed in Table 1. In particular, a commercial 65 weight percent/35 weight percent ZSM-5/ $Al_2O_3$ extrudate catalyst prepared from ZSM-5 crystals with 55/1 bulk $SiO_2/Al_2O_3$ ratio was used without further treatment. An H-form MCM-56 catalyst sample was prepared from as-synthesized MCM-56, which was crystallized in 30 gallon (113.5 L) autoclave. The as-synthesized MCM-56 with 19/1 bulk $SiO_2/Al_2O_3$ ratio was ammonium exchanged two times using ~1 M ammonium sulfate solution at an elevated temperature (49–66° C.), followed by hybrid calcination at 538° C. to remove organic templates. An H-form USY was prepared from ulktrastabilized USY with 5.4 bulk $SiO_2/Al_2O_3$ ratio and 24.54 Å unit cell size via ammonium exchange at pH 3.5 for about 4 hours to remove any non-framework aluminum species. The pH was controlled during the exchange using 20% $H_2SO4$ solution. The exchanged USY crystals were washed with water to remove residual sulfate ions, then dried and calcined in air at 538° C. for 3 hours to make an H-form USY sample. The final H-form USY sample had about 8.0 framework $SiO_2/Al_2O_3$ by $^{27}Al$ nuclear magnetic resonance (NMR) and 24.53 Å unit cell size.

TABLE 1

| | Catalyst type | | | | |
|---|---|---|---|---|---|
| | ZSM-5/ $Al_2O_3$ | MCM-56 | MCM-68 | USY | MCM-22/ $Al_2O_3$ |
| Catalyst/binder ratio | 65/35 | — | — | — | 65/35 |
| Catalyst $SiO_2/Al_2O_3$ | 55/1 | 19/1 | 18–19/1 | 8/1 | 24/1 |
| Alpha, G 102 | 230 | — | 720 | 409 | 294 |
| Alpha, G 101 | — | 141 | — | — | — |
| BET surface area ($m^2$/g) | 376 | 451 | 547 | 841 | 445 |
| zeolite surface area ($m^2$/g) | 219 | 274 | 454 | 779 | 266 |
| matrix surface area ($m^2$/g) | 157 | 177 | 93 | 62 | 179 |
| Na (ppm) | 180 | 130 | — | 4600 | 68 |
| ash (weight %) | — | 96.4 | — | 95.2 | — |
| Midas Order No. | 92-61842 | 96-62438 | 98-49711 | 98-1209 | 98-4763 |

For comparison purposes, the saturated sulfur in benzene solution was run through a reactor containing sand only (no catalyst). No reaction between sulfur and benzene was observed when the reaction was run at 300° C., 500 psig (34.0 atm), 1 WHSV.

Figure 2:
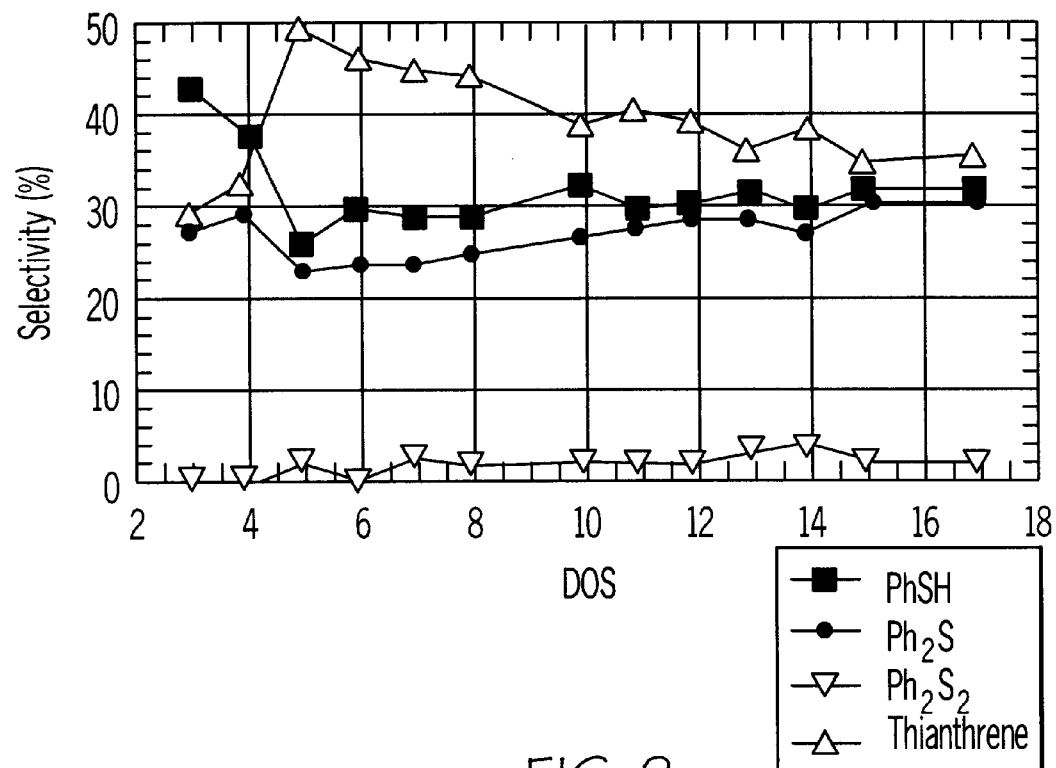
FIG. 2 is a graph showing the selectivity for thiophenol, diphenylsulfide, diphenyldisulfide, and thianthrene for the reaction and conditions of FIG. 1.
Figure 3:
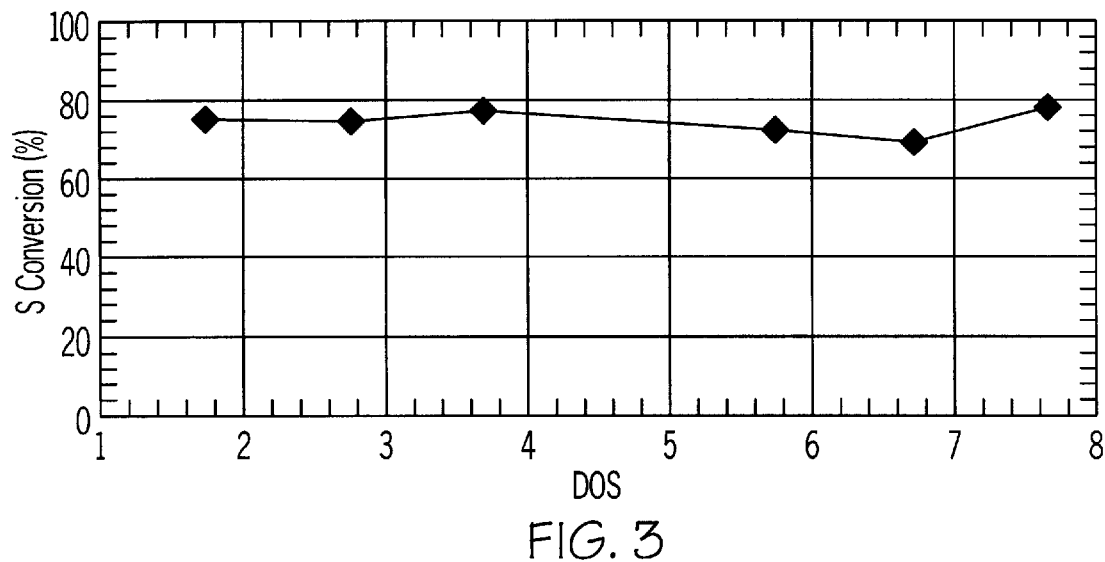
FIG. 3 is a graph showing sulfur conversion in percent as a function of days on stream (DOS) for the reaction of benzene with sulfur in the presence of ZSM-5 catalyst at 300° C., 500 psig, 1 WHSV, and a benzene to sulfur mole ratio of 20:1.
Figure 4:
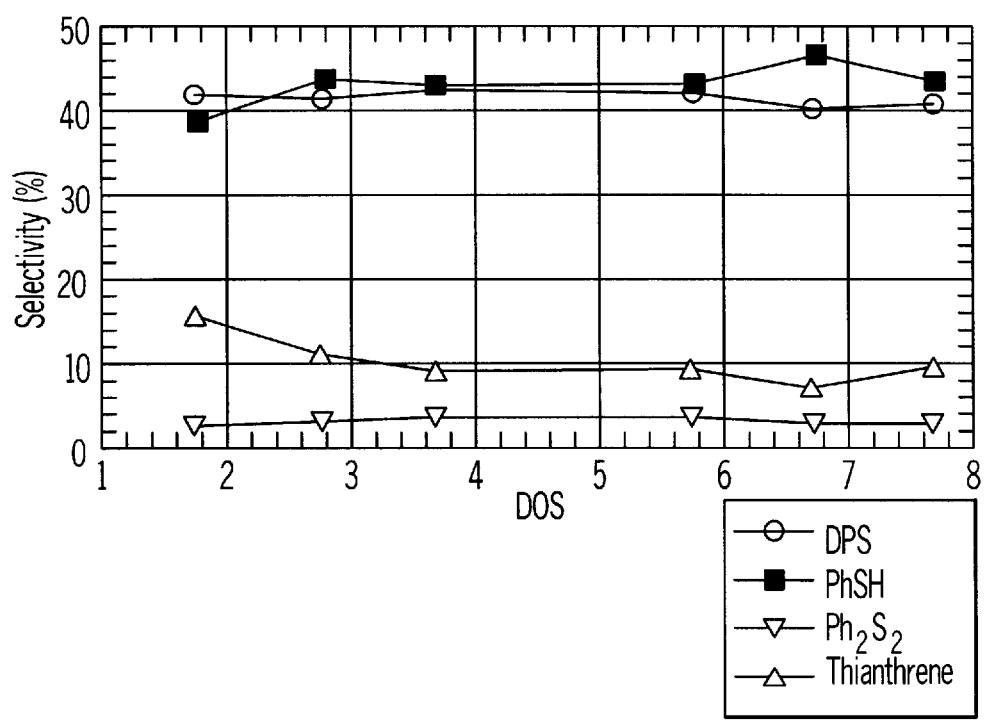
FIG. 4 is a graph showing the selectivity for thiophenol, diphenylsulfide, diphenyldisulfide, and thianthrene for the reaction and conditions of FIG. 3.
Figure 5:
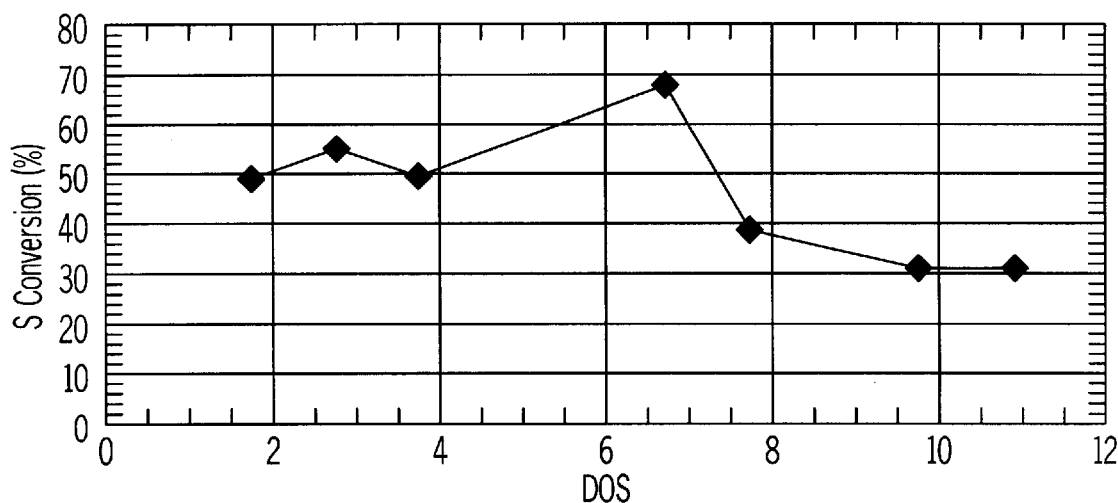
FIG. 5 is a graph showing sulfur conversion in percent as a function of days on stream (DOS) for the reaction of benzene with sulfur in the presence of MCM-68 catalyst at 300° C., 500 psig, 1 WHSV, and a benzene to sulfur mole ratio of 20:1.
Figure 6:
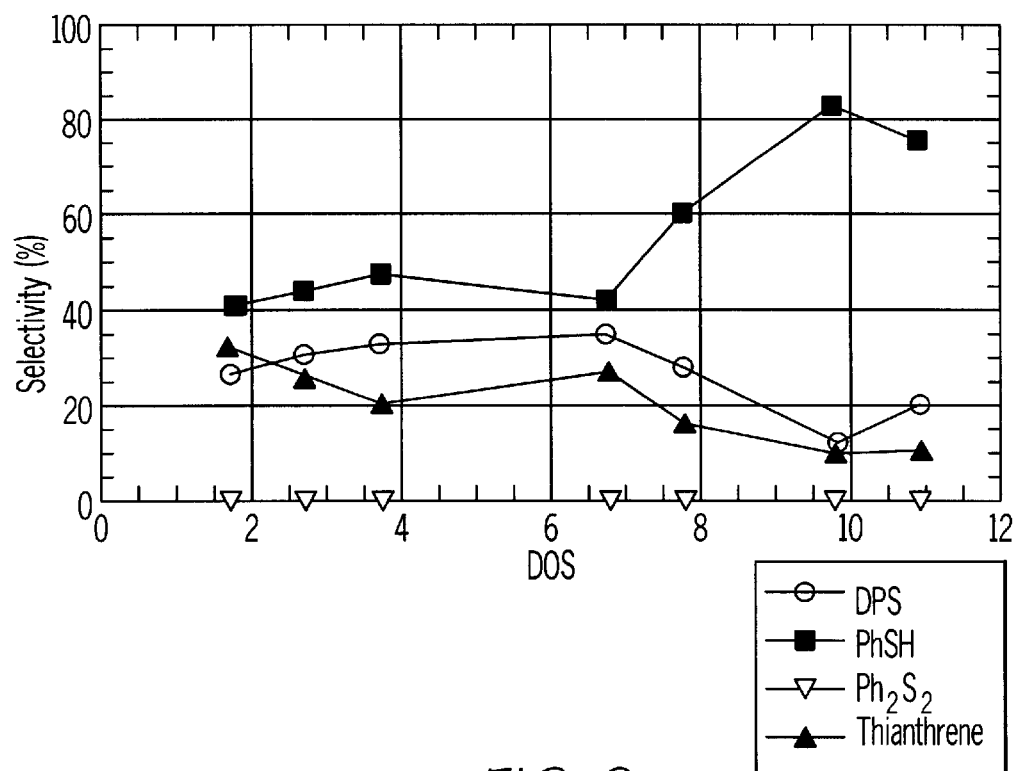
FIG. 6 is a graph showing the selectivity for thiophenol, diphenylsulfide, diphenyldisulfide, and thianthrene for the reaction and conditions of FIG. 5.
Figure 7:
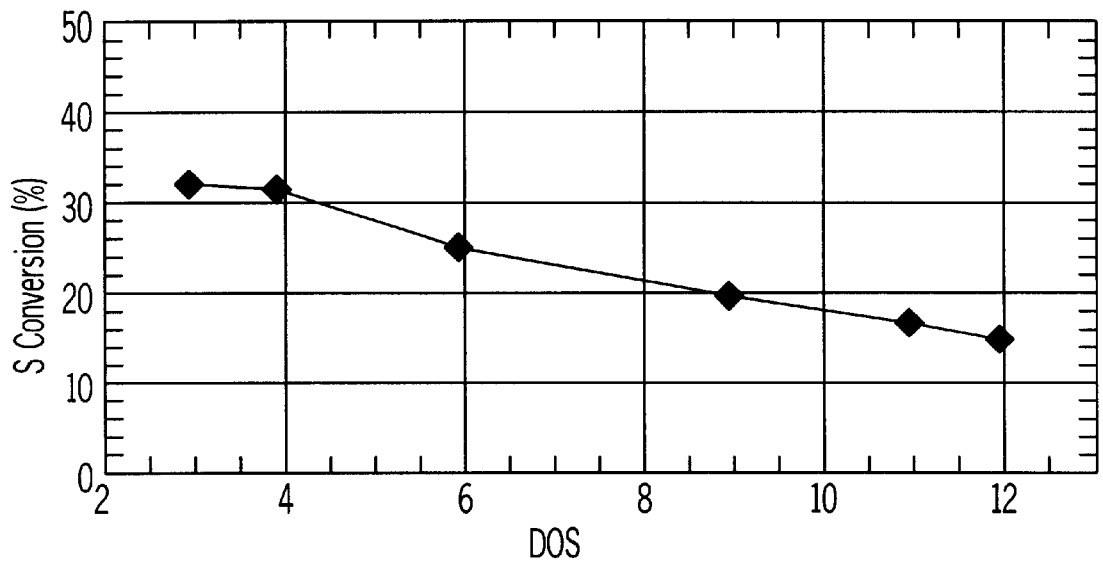
FIG. 7 is a graph showing sulfur conversion in percent as a function of days on stream (DOS) for the reaction of benzene with sulfur in the presence of USY catalyst at 300° C., 500 psig, 1 WHSV, and a benzene to sulfur mole ratio of 20:1.
Figure 8:
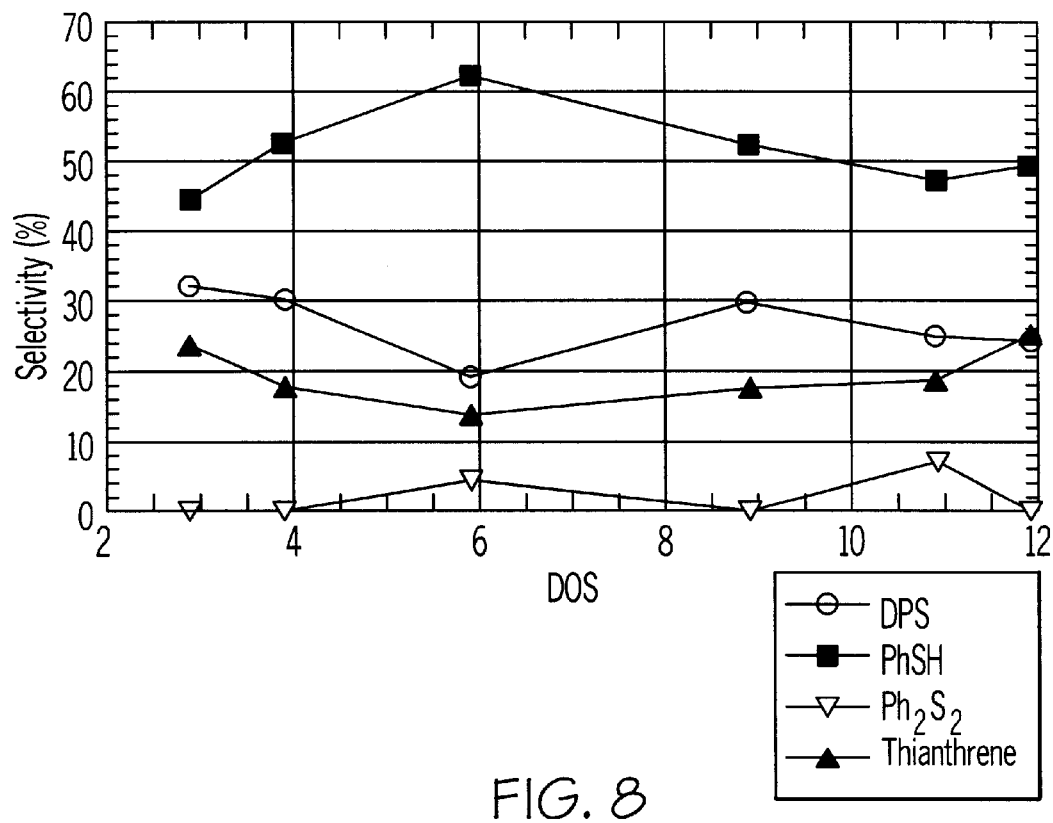
FIG. 8 is a graph showing the selectivity for thiophenol, diphenylsulfide, diphenyldisulfide, and thianthrene for the reaction and conditions of FIG. 7.

The activities of the 5 zeolite catalysts studied, plotted as the percent of sulfur conversion as a function of the number of days that the catalyst was used on the reactor strem (Days On Stream or DOS), are shown in FIGS. 1, 3, 5, 7, and 9. The selectivities of the zeolite catalysts, plotted as the percent selectivity as a function of DOS, are shown in FIGS. 2, 4, 6, 8, and 10. For convenience, the data of FIGS. 1–10 are summarized in Table 2.

TABLE 2

| | Catalyst type | | | | |
|---|---|---|---|---|---|
| | MCM-56[1] | ZSM-5 | MCM-68[2] | USY[3] | MCM-22[4] |
| sulfur conversion (%) | 100 | 74.8 | 50.9 | 31.7 | 40.6 |
| Selectivity (%) | | | | | |
| DPS | 26.8 | 42.1 | 29.8 | 30.9 | 26.0 |
| TP | 30.2 | 43.8 | 43.7 | 48.3 | 50.0 |
| TT | 40.9 | 10.6 | 26.4 | 20.8 | 24.0 |

TABLE 2-continued

| | Catalyst type | | | | |
|---|---|---|---|---|---|
| | MCM-56[1] | ZSM-5 | MCM-68[2] | USY[3] | MCM-22[4] |
| DPDS | 2.0 | 3.5 | 0 | 0 | 0 |
| DOS | 17 | 8 | 4 | 4 | 5 |

[1]Activity and selectivity data from the first two material balances (MB) were excluded from the average.
[2]Activity and selectivity data are average of the initial three MB's, which corresponds to 4 DOS.
[3]Activity and selectivity data are average of the initial two MB's, which corresponds to 4 DOS.
[4]Activity and selectivity data are average of the initial two MB's, which corresponds to 4 DOS.

The sulfur conversion data of Table 2 indicates that the catalyst activity follows the order: MCM-56>ZSM-5>MCM-68>MCM-22>USY. Differences in the accessibility of acid sites in the catalysts may account for the observed trend. MCM-56 has a unique thin-layered, open-pocket surface structure which renders most of its surface acid sites readily accessible and, accordingly, sulfur conversion is not limited by pore diffusion. In contrast, most of the acid sites in ZSM-5, MCM-68, and USY are inside the pores, so that pore diffusion may limit conversion efficiency. Further, the lower sulfur conversion for MCM-68 and USY may be caused by rapid deactivation of those catalysts, as discussed below with respect to the aging data.

The aging data in Table 2 refers to the total number of days on stream when the catalyst exhibited constant sulfur conversion and selectivity. Accordingly, the DOS data provides a measure of the catalyst stability. Among the catalysts studied, MCM-56 showed essentially no loss in sulfur conversion (100%) after 17 DOS. For ZSM-5, sulfur conversion (74.8%) remained unchanged after 8 DOS. The USY and MCM-68 catalysts both lost some activity gradually with increasing DOS. It is contemplated that the loss in activity for the USY and MCM-68 catalysts may be due to deactivation caused by the large pore sizes and low $SiO_2/Al_2O_3$ ratios for those catalysts. In particular, catalyst deactivation may be caused by the formation of oligomeric phenylenesulfides having the following structure:

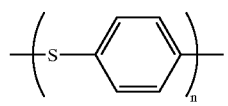

The phenylenesulfides form inside the zeolite pores and get trapped therein, thereby deactivating the catalyst. The relatively large pore sizes of the MCM-68 and USY catalysts is believed to facilitate the formation of phenylenesulfide oligomers.

The above data indicates that all five zeolites catalytically convert benzene and sulfur to diphenylsulfide, thiophenol, diphenyldisulfide, and thianthrene. Among the catalysts studied, ZSM-5 shows a higher selectivity for diphenylsulfide and thiophenol than for thianthrene. This selectivity may be attributed to a shape selectivity exhibited by the ZSM-5 catalyst.

The selectivity of MCM-22 was also determined by mixing 4 moles of benzene, 1 mole of sulfur, and 0.1 mole of MCM-22 catalyst in a round-bottom flask attached to a $N_2$ purge and a reflux condenser. The mixture was heated to reflux under the $N_2$ atmosphere. During the reaction, $H_2S$ was released through the condenser and trapped with a dilute NaOH solution. When the reaction was complete, the mixture was cooled to room temperature and then slowly added to ice-cooled water to remove any excess reactive catalyst. The water temperature was maintained at or below about 20° C. The organic layer was washed with water until neutral, dried with anhydrous sodium sulfate, and distilled to remove any unreacted benzene. The composition of the residual organic layer was determined using gas chromatography analysis. The results for the selectivity of MCM-22 are presented in Table 3. The data of Table 3 show that MCM-22 catalyst at high temperature produced 63.2% diphenyldisulfide (DPDS) and 22.7% thianthrene (TT).

TABLE 3

| g catalyst/ moles S | Temperature (° C.) | Time (hrs) | sulfur conversion (mole %) | Selectivity (%) | | | |
|---|---|---|---|---|---|---|---|
| | | | | DPS | DPDS | TT | Others |
| 10 | 80 | 16 | 3 | — | — | — | — |
| 10 | 200 | 20 | 35.8 | 4.4 | 63.2 | 22.7 | 9.7 |

The reaction of benzene and sulfur using catalytic amounts of $AlCl_3$ catalyst was also investigated. In particular, the results of changing catalyst concentration (expressed in $AlCl_3$/S mole ratio), benzene/sulfur ratios, and reaction temperature were studied. The results of those studies are presented in Tables 4–7.

TABLE 4

| Mole ratio benzene/S | Mole ratio $AlCl_3$/S | Temperature (° C.) | Time (hrs) | Sulfur conversion (mole %) | Selectivity (%) | | | |
|---|---|---|---|---|---|---|---|---|
| | | | | | DPS | DPDS | TT | Others |
| 4 | 0.1 | 80 | 4 | 44.9 | 54.8 | 7.6 | 29.9 | 7.7 |
| 4 | 0.1 | 80 | 16 | 54.5 | 27.4 | 2 | 54 | 16.6 |
| 4 | 0.25 | 80 | 6 | 59.4 | 37.9 | 4.9 | 44.8 | 12.4 |
| 4 | 0.5 | 80 | 7 | 86.9 | 72 | 2 | 18 | 8 |
| 4 | 0.83 | 80 | 5 | 86.9 | 88.9 | 3.3 | 3.8 | 4 |

TABLE 5

| Mole ratio benzene/S | Mole ratio AlCl₃/S | Temperature (° C.) | Time (hrs) | Sulfur conversion (mole %) | Selectivity (%) | | | |
|---|---|---|---|---|---|---|---|---|
| | | | | | DPS | DPDS | TT | Others |
| 10 | 0.2 | 80 | 18 | 85.4 | 60.5 | 1 | 36 | 2.5 |
| 10 | 0.35 | 80 | 18 | 93.0 | 87.6 | 0.1 | 11.7 | 0.6 |
| 10 | 0.5 | 80 | 18 | 92.7 | 94.6 | 0.4 | 4.3 | 0.7 |

TABLE 6

| Mole ratio benzene/S | Mole ratio AlCl₃/S | Temperature (° C.) | Time (hrs) | Sulfur conversion (weight %) | Selectivity (%) | | | |
|---|---|---|---|---|---|---|---|---|
| | | | | | DPS | DPDS | TT | Others |
| 2 | 0.5 | 80 | 7 | 0 | 68.6 | 4 | 24.7 | 2.7 |
| 4 | 0.5 | 80 | 18 | 77.9 | 82.7 | 0.3 | 16.2 | 0.8 |
| 4 | 0.5 | 80 | 7 | 88.8 | 74.8 | 2.9 | 16.8 | 5.5 |
| 10 | 0.5 | 80 | 18 | 92.7 | 94.6 | 0.4 | 4.3 | 0.7 |

TABLE 7

| Mole ratio benzene/S | Mole ratio AlCl₃/S | Temperature (° C.) | Time (hrs) | Sulfur conversion (mole %) | Selectivity (%) | | | |
|---|---|---|---|---|---|---|---|---|
| | | | | | DPS | DPDS | TT | Others |
| 4 | 0.5 | 50 | 7 | 0 | 58.4 | 6.2 | 12.6 | 22.8 |
| 4 | 0.5 | 50 | 18 | 69.6 | 68.7 | 5.6 | 20.5 | 5.2 |
| 4 | 0.5 | 80 | 7 | 86.9 | 72 | 2 | 18 | 8 |
| 4 | 0.1 | 80 | 4 | 44.9 | 54.8 | 7.6 | 29.9 | 7.7 |
| 4 | 0.1 | 80 | 16 | 54.5 | 27.4 | 2 | 54 | 16.6 |
| 4 | 0.1 | 120 | 5 | 63.9 | 58.6 | 6.4 | 28.7 | 6.3 |

The data in Tables 4 and 5 show that the aryl sulfide selectivities and sulfur conversion depend on AlCl₃ concentration. In particular, higher AlCl₃ concentrations favor high DPS selectivities and yields, while low catalyst concentrations favored high selectivities and yields for thianthrene (TT). The data in Table 6 show that the mole ratios of benzene/S from about 2 to about produce DPS selectivities from about 67% to about 95%, with more thianthrene (TT) being produced at lower benzene/S ratios. The data in Table 7 show that reaction temperatures ranging from about 50° C. to about 120° C. with 0.1 or 0.5 mole ratios of AlCl₃ (i.e., catalytic amounts of AlCl₃) produce high yields of DPS and TT.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true scope and spirit of the invention.

What is claimed is:

1. A method for the production of an alkylated diphenylsulfide comprising reacting an alkylated aromatic compound with elemental sulfur in the presence of at least one zeolite selected from MCM-56, ZSM-5, MCM-22, MCM-68, and USY.

2. The method of claim 1, wherein reacting the alkylated aromatic compounds with the elemental sulfur is performed in a fixed-bed reactor.

3. A method for the production of an alkylated diphenylsulfide comprising reacting an alkylated aromatic compound with elemental sulfur in the presence of a solid acid catalyst wherein the solid acid catalyst is selected from a large pore zeolite and a medium pore zeolite.

4. The method of claim 3, wherein the large pore zeolite comprises a pore structure with a ring opening of at least about 7 Å.

5. The method of claim 4, wherein the large pore zeolite is at least one zeolite selected from faujusite, zeolite X, zeolite Y, zeolite L, ZSM-4, ZSM-18, ZSM-20, and offretite.

6. The method of claim 3, wherein the medium pore zeolite comprises a pore opening less than about 7 Å and larger than about 5.6 Å.

7. The method of claim 3, wherein the medium pore zeolite comprises at least one zeolite selected from ZSM-5, ZSM-22, ZSM-23, ZSM-35, ZSM-50, ZSM-57, MCM-22, MCM-49, MCM-56, and MCM-68.

8. A method for the production of an alkylated diphenylsulfide comprising reacting an aromatic compound with elemental sulfur and an alkylating agent in the presence of a solid acid catalyst wherein the catalyst is a zeolite.

9. The method of claim 8, wherein the alkylating agent is an olefin.

10. The method of claim 3, wherein the zeolite is selected from MCM-56, ZSM-5, MCM-22, MCM-68, and USY.

11. A method for the production of an alkylated diphenylsulfide comprising reacting an aromatic compound with elemental sulfur and an alkylating agent in the presence of a solid acid catalyst, wherein the solid acid catalyst is at least one zeolite selected from a large pore zeolite and a medium pore zeolite.

12. The method of claim 11, wherein the alkylating agent is an olefin.

13. The method of claim 11, wherein the large pore zeolite is at least one zeolite selected from faujusite, zeolite X, zeolite Y, zeolite L, ZSM-4, ZSM-18, ZSM-20, and offretite.

14. The method of claim 11, wherein the medium pore zeolite is at least one zeolite selected from ZSM-5, ZSM-22, ZSM-23, ZSM-35, ZSM-50, ZSM-57, MCM-22, MCM-49, MCM-56, and MCM-68.

15. A method for the production of an arylsulfide comprising reacting an aromatic compound with elemental sulfur in the presence of a solid acid catalyst, wherein the catalyst is a medium pore zeolite catalyst.

16. The method of claim 15, wherein the medium pore zeolite is selected from ZSM-5, ZSM-22, ZSM-23, ZSM-35, ZSM-50, ZSM-57, MCM-22, MCM-49, MCM-56 and MCM-68.

17. The method of claim 15, where reacting the alkylated aromatic compound with the elemental sulfur is performed in a fixed-bed reactor.

18. The method of claim 15, where in the aromatic compound is benzene.

19. A method for the production of an arylsulfide comprising reacting an aromatic compound with elemental sulfur in the presence of a solid acid catalyst, wherein the catalyst is a large pore zeolite catalyst.

20. The method of claim 19, wherein the large pore zeolite is selected from faujusite, zeolite X, zeolite Y, zeolite L, ZSM-4, ZSM-18, ZSM-20, and offretite.

21. The method of claim 20, wherein the aromatic compound is benzene.

* * * * *